United States Patent
Harclerode et al.

(10) Patent No.: US 6,589,960 B2
(45) Date of Patent: Jul. 8, 2003

(54) HYDROMORPHONE AND HYDROCODONE COMPOSITIONS AND METHODS FOR THEIR SYNTHESIS

(75) Inventors: William H. Harclerode, Asbury, NJ (US); Robert Gault, Gross Pointe Woods, MI (US); Mark D. Sandison, Dearborn, MI (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/256,996

(22) Filed: Sep. 27, 2002

(65) Prior Publication Data

US 2003/0045720 A1 Mar. 6, 2003

Related U.S. Application Data

(62) Division of application No. 09/711,003, filed on Nov. 9, 2000, now Pat. No. 6,512,117
(60) Provisional application No. 60/164,364, filed on Nov. 9, 1999, provisional application No. 60/164,505, filed on Nov. 9, 1999, and provisional application No. 60/164,536, filed on Nov. 9, 1999.

(51) Int. Cl.$^7$ ................ A61K 31/485; C07D 489/00
(52) U.S. Cl. ............................................. 514/282; 546/45
(58) Field of Search ............................ 514/282; 546/45

(56) References Cited

FOREIGN PATENT DOCUMENTS

WO          98/05667      *  2/1998    ................ 546/45

* cited by examiner

*Primary Examiner*—Charanjit S. Aulakh
(74) *Attorney, Agent, or Firm*—Lahive & Cockfield, LLP; Peter C. Lauro; Guilio A. DeConti, Jr.

(57) ABSTRACT

A method for the preparation of a ketone from a narcotic alkaloid having an allyl alcohol moiety is disclosed. The method includes mixing the narcotic alkaloid with an acid in the presence of a catalyst wherein the method is carried out in the substantial absence of hydrogen gas. The method is useful for preparing hydromorphone and hydrocodone compositions having novel impurity profiles. Compositions comprising hydromorphone and hydrocodone are also disclosed.

29 Claims, No Drawings

HYDROMORPHONE AND HYDROCODONE COMPOSITIONS AND METHODS FOR THEIR SYNTHESIS

RELATED APPLICATIONS

This application is a divisional application of application Ser. No. 09/711,003, filed on Nov. 9, 2000, now U.S. Pat. No. 6,512,117, Issuing, that claims priority to application No. 60/164,364, filed on Nov. 9, 1999, application No. 60/164,505, filed on Nov. 9, 1999, and application No. 60/164,536, filed on Nov. 9, 1999. The contents of all of the aforementioned applications are hereby incorporated by reference.

BACKGROUND OF THE INVENTION

Hydromorphone hydrochloride (sold as Dilaudid, Laudicon, Hydromorphan) is a narcotic analgesic and one of its principle uses is the relief of pain (Physicians Desk Reference, p. 1383; Merck Index, 4700). The precise mechanism of hydromorphone hydrochloride is not known, although it is believed to relate to the existence of opiate receptors in the central nervous system. There is no intrinsic limit to the analgesic effect of hydromorphone hydrochloride; like morphine, adequate doses will relieve even the most severe pain.

Hydromorphone hydrochloride is also a centrally acting narcotic antitussive which acts directly on the cough reflex center. In addition, it produces drowsiness, changes in mood and mental clouding, depresses the respiratory center, stimulates the vomiting center, produces pinpoint constriction of the pupil, enhances parasympathetic activity, elevates cerabrospinal fluid pressure, increases biliary pressure and also produces transient hyperglycemia.

Hydrocodone (dihydrocodeinone, Bekadid, Dicodid) is a semisynthetic narcotic antitussive and analgesic with multiple actions similar to those of codeine. Like hydromorphone and other opiate compounds, the mechanism of action is not known. Hydrocodone can produce meoisis, euphoria, and physical and physiological dependence. In excessive doses, hydrocodone depresses respiration (Physicians Desk Reference, p. 948).

The syntheses of hydromorphine and hydrocodeine are known in the art. For example, the formation of hydromorphine from morphine via room temperature hydrogenation of the double bond with colloidal palladium and hydrogen gas is disclosed in German Patent 260 233. The patent also discloses the formation of hydrocodeine. Yields of the hydrogenated derivatives are not disclosed.

In United Kingdom Patent No. 285,404, the formation of dihydrotheibane (a dimethyl ether derivative of dihydromorphine) at room temperature is disclosed, using platinum oxide as the catalyst. The methyl groups can be removed to yield dihydromorphine. The yield is approximately 55%.

The syntheses of hydrocodone and hydromorphone from codeine and morphine, respectively, are also known in the art.

German Patent 380 919 discloses a method for synthesizing hydromorphone, by treating morphine with a catalytic agent (e.g., platinum or palladium black), hydrochloric acid, and hydrogen gas. The reaction mixture is then heated to 60 to 90° C. under a water pressure of 30 cm. The yield of the ketone is not disclosed.

German Patent 607 931 discloses the synthesis of hydromorphinones. The synthesis involves heating morphine with large amounts of finely divided platinum in dilute acid. The platinum catalyst is saturated with hydrogen gas before the reaction is begun. It was found that additional hydrogen gas was not necessary for the hydrogenation to proceed. Yields from 40% to 85% were reported.

German Patent 617 238, a continuation-in-part of German Patent 607 931, discloses that relatively higher yields of the hydromorphones can be obtained through using smaller amounts of catalyst. The resulting yields ranged from 70% to 95% of the theoretical yield.

U.S. Pat. No. 2,544,291 discloses a process for the preparation of dihydrocodone by treating codeine with supported palladium catalyst in a heated acidic solution. The reaction mixture is purified through treatment with activated alumina. The resulting product was recovered in 66.5% yield and was determined to be "codeine free."

U.S. Pat. No. 2,628,962 discloses the oxidation of dihydrocodeine to dihydrocodone by the addition of ketones to the reaction mixture in the presence of aluminum alkoxides. The resulting yield was 36.5%.

U.S. Pat. No. 2,654,756, a continuation-in-part of U.S. Pat. No. 2,628,962, discloses the use of ketones, such as cyclohexanone and alkoxycyclohexanones, to increase the yield of the narcotic ketones from the corresponding alcohols in the presence of aluminum alkoxides. However, the resulting yields were approximately 40%.

U.S. Pat. No. 2,649,454 discloses a method of producing ketone derivatives of opiates by heating the alcohols in the presence of potassium t-butoxide. The yields of the reaction ranged from 71–83%.

Most recently, it was reported that it was possible to form dihydroketones from narcotic alkaloids with colloidal platinum or palladium as the catalyst. It was noted that if hydrogen was not introduced, the reaction could be carried out in the presence of a larger amount of finely divided platinum. However, it was reported that the purest products or the most easily purified products were obtained when the reaction was performed in a stream of hydrogen, rather than in the absence of hydrogen (Gaal, C. M.T.A. Kemai Oszt. Kozl. 24:307–313 (1965)).

SUMMARY OF THE INVENTION

In one aspect, the invention features a method of preparing a ketone from a narcotic alkaloid having an allyl alcohol moiety. The method comprises mixing the narcotic alkaloid with an acid in the presence of a catalyst in the substantial absence of hydrogen gas. Advantageously, the narcotic alkaloid is morphine, codeine or salts thereof.

Preferably, the narcotic alkaloid is of formula (I):

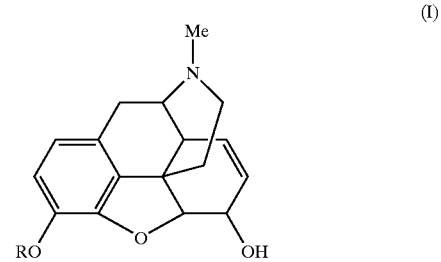

wherein R is hydrogen or, an alcohol protecting moiety. In an advantageous embodiment, R is hydrogen or methyl.

The invention also pertains to a hydromorphone composition that is substantially free of impurities. In an advantageous embodiment, the composition comprises hydromorphone and from about 0.05% up to about 1.0% dihydromorphine; up to about 0.1% morphine; up to about 0.8% 8-hydroxy hydromorphone; up to about 0.5% bis-hydromorphone; and up to about 0.2% other impurities.

In another aspect, the invention is directed to a method of forming a pharmaceutical composition comprising a hydromorphone salt, 8-hydroxy hydromorphone and dihydromorphone. The method comprises heating an aqueous mixture of the salt, 8-hydroxy hydromorphone and dihydromorphone for a time sufficient to reduce the concentration of 8-hydroxy hydromorphone to less than 1.0%. In yet another aspect, the invention is directed to a hydromorphone composition which is prepared by a process, which includes mixing morphine with an acid in the presence of a catalyst wherein said process is carried out in the substantial absence of hydrogen gas.

DETAILED DESCRIPTION OF THE INVENTION

The invention pertains to a method of synthesizing ketone derivatives of narcotic alkaloids by mixing the narcotic alkaloid with an acid in the presence of a catalyst in the substantial absence of hydrogen gas. The product obtained from the methods of the invention has a novel composition profile, discussed in detail below.

1. DEFINITIONS

Before further description of the invention, certain terms employed in the specification, examples and appended claims are, for convenience, collected here.

The term "alcohol protecting moiety" includes moieties which can be removed and/or derivatized after the formation of the ketone in accordance with the methods of the invention to yield the free alcohol. Advantageously, the alcohol protecting moiety is inert to the conditions used to generate the ketone. Alcohol protecting moieties include, but are not limited to, hydroxyl protecting groups known in the art (see, for example, Greene, T. W. *Protective Groups in Organic Synthesis* (Wiley:New York, 1981)). Examples include methoxymethyl ethers (MOM), β-methoxyethoxymethyl ethers (MEM), tetrahydropyranyl ethers (THP), methylthiomethyl ethers (MTM), benzyl groups, and silyl ethers (e.g., trimethyl silyl ethers (TMS), t-butyldimethyl silyl ethers (TBDMS)). Furthermore, the term "alcohol protecting moiety" includes alkyl, alkenyl, alkynyl, aralkyl, aryl, and heteroaryl moieties.

The term "alkenyl" includes unsaturated aliphatic groups analogous in length and possible substitution to the alkyls described below, but that contain at least one double bond. Unless the number of carbons is otherwise specified, "lower alkenyl" refers to an alkenyl group, as defined above, but having from two to four carbon atoms in its backbone structure.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include heteroatoms replacing one or more carbons of the hydrocarbon backbone, e.g., oxygen, nitrogen, sulfur or phosphorous atoms. In one embodiment, a straight chain or branched chain alkyl has 20 or fewer carbon atoms in its backbone (e.g., $C_1$–$C_{12}$ for straight chain, $C_3$–$C_{12}$ for branched chain). Examples of alkyl groups contemplated by the invention include, but are not limited to, methyl, ethyl, isopropyl, isobutyl, tert-butyl, branched pentyl, branched hexyl, cyclohexyl, and cyclopentyl groups.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), arylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the substituents on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). Unless the number of carbons is otherwise specified, "lower alkyl" refers to an alkyl group, as defined above, but having from one to three carbon atoms in its backbone structure. The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkynyl" includes unsaturated aliphatic groups analogous in length and possible substitution to the alkyls described above, but that contain at least one triple bond. Unless the number of carbons is otherwise specified, "lower alkynyl" refers to an alkynyl group, as defined above, but having from two to four carbon atoms in its backbone structure.

The term "allyl alcohol moiety" includes hydroxyl moieties located on allylic carbons, e.g., on carbons adjacent to double bonds.

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin). The term "aralkyl" includes alkyl groups substituted with at least one aryl group and aryl groups substituted with at least one alkyl group.

The term "Deutsches Arzneibuch ('DAB') Test" refers to a battery of tests for confirming the identification of and establishing a purity standard for a pharmaceutical. A pharmaceutical is deemed to pass the DAB battery of tests in accordance with the following protocol:

MATERIALS AND METHODS

For the DAB protocol, the test solution is made by dissolving 1.25 g of the test substance in 25 mL of water.

PART 1: IDENTIFICATION

Characteristics

The test compound should be a white crystalline powder; slightly soluble in water, soluble in about 30 parts 90% ethanol; and not very soluble in chloroform.

Test A

The Infrared (IR) Absorbtion Spectrum (Pharm. Eur. test V.6.18) of the precipitate from Test D is compared with the spectrum of a pharmaceutical reference of known identity. Both the absorbtion maxima and the relative intensities are compared to reference spectra.

Test B 2 to 3 mg of the test substance are dissolved in 3 ml of ice-cooled formaldehyde-sulfuric acid. The color of solution should turn from yellow to violet.

Test C 1 mL of the test solution is diluted to 25 mL with water. To 5 mL of the diluted solution, is added 0.3 mL of potassium iodate solution and 0.4 mL of 7% solution of hydrochloric acid. The solution immediately turns yellow. When 0.5 mL of a 10% ammonia solution is added, the yellow color should become deeper.

Test D 1 mL of a 10% ammoniac solution is added to 3mL of the test solution. After the solution was rubbed with a glass rod, a white crystalline precipitate is formed. The precipitate is washed with water and dried at a temperature of 100 to 105° C. The precipitate should melt at a temperature between 263 and 268° C (see Pharm. Eur. Test V.6.11.3, Melting Point-instantaneous method).

Test E

The filtrate of D should give the identity reaction of chlorides (V.3.1.1).

PART 2: TESTING OF PURITY

Appearance of Test Solution

The test solution must be clear (V.6.1) and colorless (V.6.2., Method II).

Acidity or Alkalinity 2 mL of the test solution should not develop a yellow color after the addition of 0.05 mL of methyl red solution. Also, a 2 mL solution of the test solution should not develop a yellow color after the addition of 0.05 mL of a Bromcresol green solution.

Specific Optical Rotation (V.6.6)

The optical rotation of the test solution should be between −136.5° and −138.5° and should be calculated with reference to the dried substance.

Alkaloids without Phenolic Hydroxyl Group 1.0 mL test solution should not become turbid after dilution with 1.2 mL water and dropwise addition of 1.2 mL of an 8.5% NaOH solution.

Reactivity with Sulphuric Acid ("Readlily Carbonizable Substance Test")

20 mg of the test substance is dissolved in 5 mL of 96% sulphuric acid. After 5 minutes, the solution should not be more strongly colored than the comparative solution BG6 (V.6.2, Method I).

Morphine and Non-hydrated Morphine Related Substances

The test solution from the "Reactivity with Sulphuric Acid" test should not become green or blue colored after the addition of 0.2 mL of Ferric (III)-chloride solution, and after heating in a water bath for 1 minute.

Loss on Drying

When 1.000 g of test substance is dried in an oven at 100 to 105° C., not more than 0.5% of the total weight should be lost (V.6.22).

Sulphated Ash

Not more than 0.1%, as determined from 0.100 g of the test substance (V.3.2.14).

Assay 0.200 g of test substance was dissolved in a mixture of 5 mL of water, 30 mL of ethanol, and 10 mL of chloroform. After the addition of 0.5 mL of Bromothymol Blue solution, the test substance solution is titrated, with agitation, with a 0.1 N NaOH until the solution turns light green.

1 mL of 0.1 NaOH solution is equivalent to 32.18 mg of $C_{17}H_{20}ClNO_3$.

One of the purity tests included in the DAB battery of tests is the "Reactivity with Sulphuric Acid Test", which is also known in the art as the "Readily Carbonizable Substances Test".

The term "heteroatom" includes atoms of any element other than carbon or hydrogen. Preferred heteroatoms are nitrogen, oxygen, sulfur and phosphorus.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino; arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "narcotic alkaloid" includes organic nitrogenous bases and their salts. It includes alkaloids derived from opiates, e.g., morphine and codeine. The term includes alkaloids containing allylic alcohols which advantageously may be converted to ketones using the methods of the invention.

The term "non-supported" includes catalysts which are not deposited on a substrate (e.g., alumina, pumice or charcoal). Examples of non-supported catalysts include palladium catalysts such as palladium black.

The term "substantial absence" of hydrogen gas refers to reaction conditions where the amount of hydrogen gas in the reaction vessel is, for example, less than 5%, less than 2%, or, preferably, less than 1%.

The term "substantially free of impurities" refers to compositions of the invention containing impurities (e.g., in the case of hydromorphone, reaction by-products including dihydromorphine, morphine, 8-hydroxy hydromorphone, bis-hydromorphone, and other unspecified impurities) which are absent or present in the composition in amounts such that the composition passes the Readily Carbonizable Substances Test and/or the Deutsches Arzneibuch Test.

2. METHODS

The invention pertains, at least in part, to a method for preparing a ketone from a narcotic alkaloid having an allyl alcohol moiety. The method comprises mixing the narcotic alkaloid with an acid in the presence of a catalyst in the substantial absence of hydrogen gas.

Scheme 1 shows an example of a synthetic method of the invention. (See Examples 1–4 below for a more detailed experimental discussion.) Briefly, water, concentrated HCl and activated palladium catalyst are added to a reaction vessel under a nitrogen atmosphere and heated to 95° C. The narcotic alkaloid is then added and the reaction temperature is maintained. After an hour, the reaction mixture is filtered to remove the catalyst and then cooled to 40° C. and sodium metabisulfite is added. The solution is then allowed to cool to room temperature and stirred overnight. The sulfite adduct is then heated to reflux in water with activated charcoal. After approximately ten minutes, the activated charcoal is removed by filtration. Sodium carbonate is then added and the pH of the solution is adjusted to above its pKa, preferably, 9.0–9.5, with concentrated ammonium hydroxide. After stirring overnight, the suspension is filtered, converted to one of its salt, e.g., HCl salt, and the narcotic alkaloid ketone is dried under vacuum. In another embodiment of the invention, the sulfite adduct is heated for five hours in deionized water (see Example 4) before the addition of sodium carbonate.

In one embodiment, the narcotic alkaloid comprises a compound represented by formula (I):

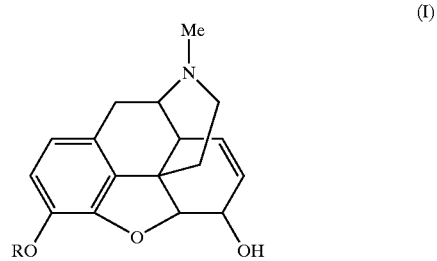

(I)

wherein R is hydrogen or an alcohol protecting moiety. Preferably, R is alkyl (e.g., lower alkyl, more preferably methyl), aralkyl, or aryl. In one embodiment, the narcotic alkaloid is morphine (R=H) or codeine (R=CH$_3$), or a salt thereof. In another embodiment, the alcohol protecting moiety is removed upon formation of the ketone.

SCHEME 1

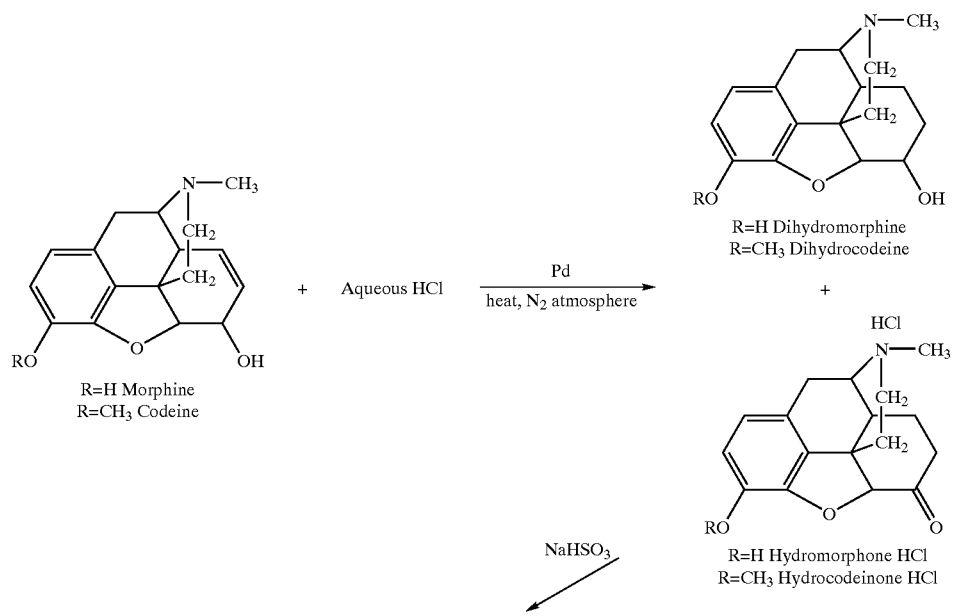

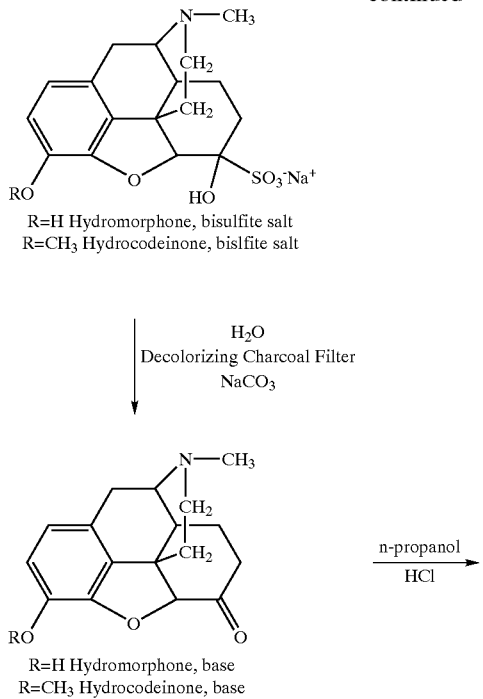

R=H Hydromorphone, bisulfite salt
R=CH₃ Hydrocodeinone, bislfite salt

| H₂O
| Decolorizing Charcoal Filter
| NaCO₃
↓

R=H Hydromorphone, base
R=CH₃ Hydrocodeinone, base

→ n-propanol HCl →

R=H Hydromorphone, hydrochloride
R=CH₃ Hydrocodeinone hydrochloride

In another embodiment, the ketone comprises a compound represented by the formula II:

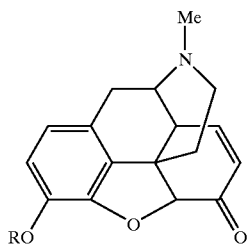

(II)

wherein R is as defined above. Advantageously, R is H or CH₃.

In one embodiment, the ketone is hydromorphone or one of its salts. In yet another embodiment, the method further comprises heating the mixture for a period of time sufficient to yield a hydromorphone composition comprising less than 1.0% 8-hydroxy hydromorphone. Preferably the period of time is greater than about thirty minutes, more preferably greater than about three hours, and still more preferably greater or equal to about five hours.

The hydromorphone composition prepared by the methods of the invention is substantially free of impurities. In certain embodiments, the hydromorphone composition contains the following impurities: about 0.05% dihydromorphine; about 0.0% morphine; about 0.0% 8-hydroxy hydromorphone; about 0.0% bis-hydromorphone; and about 0.0% other impurities. In yet other embodiments, the hydromorphone composition contains up to about 1.0% dihydromorphine; up to about 0.1% morphine; up to about 0.8% 8-hydroxy hydromorphone; up to about 0.5% bis-hydromorphone; and up to about 0.2% other impurities In a further embodiment, the hydromorphone synthesized by methods of the invention passes the Readily Carbonizable Substances Test and/or the Deutsches Arzneibuch Test (see Example 5).

In another embodiment, the ketone is hydrocodone or one of its salts. The hydrocodone prepared by the methods of the invention is substantially free of impurities. In one embodiment, the hydrocodone synthesized by methods of the invention passes the Readily Carbonizable Substances Test and/or the Deutsches Arzneibuch Test (See Example 5).

The acid used in the methods of the invention can be any acid which allows for the formation of the ketone. Examples of suitable acids include, but are not limited to carbonic acid, sulfuric acid, phosphoric acid, hydrobromic acid, acetic acid, and, preferably, hydrochloric acid. Many other suitable acids are well known in the art.

The catalyst used in the methods of the invention can be any catalyst which catalyzes the formation of the ketone from the allylic acid alcohol of the narcotic alkaloid. Examples of suitable catalysts include, but are not limited to, platinum and, preferably, palladium. In a preferred embodiment, an non-supported catalyst, e.g., palladium black, as opposed to a supported catalyst, e.g., palladium on alumina, pumice or charcoal, is used.

3. COMPOSITIONS

In another aspect, the invention features a composition comprising hydromorphine. The hydromorphone composition of the invention is substantially free of impurities. In certain embodiments, the hydromorphone composition contains the following impurities: about 0.05% dihydromorphine; about 0.0% morphine; about 0.0% 8-hydroxy hydromorphone; about 0.0% bis-hydromorphone; and about 0.0% other impurities. In yet other embodiments, the hydromorphone composition contains up to about 1.0% dihydromorphine; up to about 0.1% morphine; up to about 0.8% 8-hydroxy hydromorphone; up to about 0.5% bis-hydromorphone; and up to about 0.2% other impurities In a further embodiment, the composition contains from about 0.05% up to about 0.5% dihydromorphine. In another embodiment, the composition contains up to about 0.05% morphine (e.g., from about 0.0% up to about 0.05% morphine). In yet another embodiment, the composition comprises up to about 0.5% 8-hydroxy hydromorphone (e.g., from about 0.0% up to about 0.5% 8-hydroxy hydromorphone). In another embodiment, the composition contains up to about 0.05% bis-hydromorphone (e.g., from about 0.0% up to about 0.05% bis-hydromorphone). In a further embodiment, the composition contains up to about 0.1% other impurities (e.g., from about 0.0% up to about 0.1% other impurities).

Preferably, the composition comprises hydromorphone and from about 0.22% up to about 0.29% dihydromorphine; up to about 0.02% morphine (e.g., from about 0.0% up to about 0.02% morphine); from about 0.04% up to about 0.05% 8-hydroxy hydromorphone; up to about 0.02% bis-hydromorphone (e.g., from about 0.0% up to about 0.02% bis-hydromorphone); and up to about 0.06% other impurities (e.g., from about 0.0% to about 0.06% other impurities).

In a particularly preferred embodiment, the composition comprises hydromorphone and about 0.26% dihydromorphine; about 0.01% morphine; about 0.04% 8-hydroxy hydromorphone; about 0.02% bis-hydromorphone; and about 0.06% other impurities.

Preferably, the compositions of the invention passes the Readily Carbonizable Substances Test and/or the Deutsches Arzneibuch Test (see Example 5). Advantageously, the invention pertains to a hydromorphone composition of the invention which is prepared by mixing morphine with an acid (e.g., hydrochloric acid) in the presence of a catalyst (e.g., non-supported palladium) in the substantial absence of hydrogen gas. Methods of synthesizing the composition of the invention are discussed in Examples 1–4 and in Scheme 1. Preferably, the composition passes the Readily Carbonizable Substances Test and/or the Deutsches Arzneibuch Test.

4. PHARMACEUTICAL COMPOSITIONS

The invention also pertains to a method of forming a pharmaceutical composition comprising a hydromorphone salt, 8-hydroxy hydromorphone and dihydromorphone. The method includes heating an aqueous mixture of the salt, 8-hydroxy hydromorphone and dihydromorphine for a time sufficient to reduce the concentration of 8-hydroxy hydromorphone to less than 1.0%. In one embodiment, the time is greater than about thirty minutes, more preferably greater than about three hours, and still more preferably greater than or equal to about five hours. In one embodiment, the salt is bisulfite. Advantageously, the pharmaceutical composition contains hydromorphone and about 0.05% up to about 1.0% dihydromorphine; about 0.0% up to about 0.1% morphine; about 0.0% up to about 0.8% 8-hydroxy hydromorphone; about 0.0% up to about 0.5% bis-hydromorphone; and about 0.0% up to about 0.2% other impurities. Preferably, the composition passes the Readily Carbonizable Substances Test and/or the Deutsches Arzneibuch Test (see Example 5).

EXEMPLIFICATION OF THE INVENTION

The invention is further illustrated by the following examples which should not be construed as limiting. The palladium catalyst used in the following examples was activated in accordance with the following procedure.

Palladium Activation Procedure

Palladium black (36.0 g) and deionized (DI) water (36.0 g) were sonicated to break down larger catalyst agglomerations. DI water (500 mL) and concentrated HCl (120 mL) were added. The nitrogen flow was adjusted to 1.4 mL/min and the suspension was heated. When the suspension reached 50° C., the nitrogen flow was stopped and a hydrogen flow of 1.0 mL/min was initiated. The suspension was heated at 85° C. for two hours, cooled and filtered through Whatman #542 paper. The preparation of "hydrogen-free" catalyst used the same procedure, except for the omission of hydrogen.

EXAMPLE 1

Synthesis of Hydromorphone Hydrochloride—"Current Process"

DI water (49.0 g), concentrated HCl (12.0 g), and activated palladium catalyst (3.6 g) were charged to the reactor. The reactor was padded with nitrogen and heated to 50° C. The nitrogen was then turned off and the hydrogen flow was set to 0.2 mL/min. When the suspension reached 95° C., morphine hydrate (40.0g) was added to the reactor. The reaction mixture was maintained at 95° C. for one hour. The reaction mixture was cooled to 40° C. and sodium metabisulfite (26.4 g) was added. The suspension was allowed to cool to room temperature and stirred overnight. The resulting sulfite adduct (30.3 g, dry weight; 59% yield) was filtered and dried under vacuum.

The sulfite adduct (30.0 g) and DI water (430 g) were heated to reflux and 0.2 g of activated charcoal was added. The activated charcoal was filtered after fifteen minutes. Sodium carbonate (12.6 g) was added to the filtrate and the pH of the solution was adjusted to 9.0 with concentrated ammonium hydroxide (6 mL). After stirring overnight, the suspension was filtered and the hydromorophone base (15.6 g, dry weight; 41% yield) was dried under vacuum.

The hydromorphone base (15.0 g) was dissolved in methanol/DI water (14 mL, 50/50 by volume) and concentrated HCl/water (10 mL, 50/50 by volume). The solution was filtered and n-propanol (42 mL) was added. The suspension was stirred overnight, filtered, and vacuum dried. The dried hydromorphone hydrochloride (12.9 g; 30% yield) contained 0.7% 8-hydroxyhydromorphone and 0.1 % dihydromorphine. The hydromorphone hydrochloride failed the Readily Carbonizable Substances Test.

EXAMPLE 2

"Hydrogen Free" Synthesis

The above synthesis was repeated, except that hydrogen was replaced with nitrogen in the palladium black activation procedure and during the reaction. The hydromorphone hydrochloride product was obtained in the same yield and had the following impurity profile: 0.6% 8-hydroxyhydromorphone and 0.2% dihydromorphine. The hydromorphone hydrochloride failed the Readily Carbonizable Substances Test.

EXAMPLE 3

"Extra Heating Time" Synthesis

Sulfite adduct was prepared using the current process using hydrogen. This sulfite adduct (10.0 g) and DI water (140 g) were heated to reflux for five hours. The solution was cooled and sodium carbonate (4.1 g) was added. The pH of the solution was adjusted to 8.8 with concentrated ammonium hydroxide (1.8 mL). After stirring overnight, the suspension was filtered, and the hydromorphone base (4.6 g, dry weight) was dried under vacuum.

The hydromorphone base (4.0 g) was dissolved in methanol/DI water (4 mL, 50/50 by volume) and concentrated HCl/water (3 mL, 50/50 by volume). The solution was filtered and n-propanol (18 mL) was added. The suspension was stirred overnight, filtered, and vacuum dried. The dried hydromorphone hydrochloride (3.0 g) contained <0.1% 8-hydroxyhydromorphone and 0.25 dihydromorphine. The hydromorphone hydrochloride passed the Readily Carbonizable Substances Test.

EXAMPLE 4

"Hydrogen Free/Extra Heating Time" Synthesis

Sulfite adduct was prepared without using hydrogen. The sulfite adduct (12.0 g) and DI water (184 g) were heated to reflux for 5 hours. The solution was cooled and sodium carbonate (4.9 g) was added. The pH of the solution was adjusted to 8.8 with concentrated ammonium hydroxide (2 mL). After stirring overnight, the suspension was filtered and the hydromorphone base (6.4 g, dry weight) was dried under vacuum.

The hydromorphone base (6.0 g) was dissolved in methanol/DI water (6 mL, 50/50 by volume) and concentrated HCl/water (4.4 mL, 50/50 by volume). The solution was filtered and n-propanol (27 mL) was added. The suspension was stirred overnight, filtered, and vacuum dried. The dried hydromorphone hydrochloride (5.1 g) contained <0.1% 8-hydroxyhydromorphone and 0.25 dihydromorphine. The hydromorphone hydrochloride passed the Readily Carbonizable Substances Test.

EXAMPLE 5

HPLC Detection and Quantitation of Impurities

The detection and quantitation of impurities in hydromorphone compositions is carried out using a gradient high pressure liquid chromatography (MPLC) method. An aqueous solution of the hydromorphone composition is injected onto a Waters Symmetry C18 column (3.9 mm×150 mm) which contains 5 µm particles. A gradient elution is run at 1 mL per minute. Elution begins with eluent that contains 90% mobile phase A and 10 % mobile phase B, and ends, after a 40 minute run time, with eluent that contains 20% mobile phase A and 80% mobile phase B. The mobile phase A includes 1 g of heptane sulfonic acid, 1 mL triethylamine, and 90/10 water/methanol solvent to increase the volume of the solution to 1 liter. The pH of mobile phase A is adjusted to 2.5 by the addition of phosphoric acid. Mobile phase B is a 50/50 water/methanol mixture. The pH of mobile phase B is adjusted to 2.5 with phosphoric acid. The method is used to resolve and quantitate 8-hydroxyhydromorphone, morphine, dihydromorphine, hydromorphone N-oxide, hydromorphone, and 2,2-bishydromorphone.

INCORPORATION BY REFERENCE

The entire contents of all patents, published patent applications and other references cited herein are hereby expressly incorporated herein by reference

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A composition comprising hydromorphone and:
   a) from about 0.05% up to about 1.0% dihydromorphine;
   b) up to about 0.1% morphine;
   c) up to about 0.8% 8-hydroxy hydromorphone;
   d) up to about 0.5% bis-hydromorphone; and
   e) up to about 0.2% other impurities.

2. The composition of claim 1, comprising from about 0.05% up to about 0.5% dihydromorphine.

3. The composition of claim 1, comprising from about 0.0% up to about 0.05% morphine.

4. The composition of claim 1, comprising from about 0.0% up to about 0.5% 8-hydroxy hydromorphone.

5. The composition of claim 1, comprising from about 0.0% up to about 0.05% bis-hydromorphone.

6. The composition of claim 1, comprising from about 0.0% up to about 0.1 % other impurities.

7. A composition comprising hydromorphone and:
   a) from about 0.22% up to about 0.29% dihydromorphine;
   b) up to about 0.02% morphine;
   c) from about 0.04% up to about 0.05% 8-hydroxy hydromorphone;
   d) up to about 0.02% bis-hydromorphone; and
   e) up to about 0.06% other impurities.

8. A composition comprising hydromorphone and about 0.26% dihydromorphine; about 0.01% morphine; about 0.04% 8-hydroxy hydromorphone; about 0.02% bis-hydromorphone; and about 0.06% other impurities.

9. The composition of any one of claims 1, 7, or 8, wherein said composition is prepared by a process comprising mixing morphine with an acid in the presence of a catalyst wherein said process is carried out in the substantial absence of hydrogen gas.

10. The composition of claim 9, wherein said process further comprises heating said mixture for a period of time sufficient to yield a hydromorphone composition comprising less than about 1.0% 8-hydroxy hydromorphone.

11. The composition of claim 10, wherein said period of time is sufficient to yield a hydromorphone composition comprising less than or equal to 2.0% dihydromorphine.

12. The composition of claim 10, wherein said time is greater than about thirty minutes.

13. The composition of claim 10, wherein said time is greater than or equal to about five hours.

14. The composition of claim 9, wherein said acid is hydrochloric acid and said catalyst is non-supported palladium.

15. A composition comprising hydromorphone, from about 0.05% up to about 1.0% of dihydromorphine, and one or more compounds selected from the group consisting of morphine, 8-hydroxy hydromorphone, bis-hydromorphone, and other impurities.

16. A hydromorphone composition which is substantially free of impurities.

17. The composition of claim 16, which comprises:
   a) from about 0.05% up to about 1.0% dihydromorphine;
   b) up to about 0.1% morphine;
   c) up to about 0.8% 8-hydroxy hydromorphone;
   d) up to about 0.5% bis-hydromorphone; and
   e) up to about 0.2% other impurities.

18. A method of forming a pharmaceutical composition comprising a hydromorphone salt, 8-hydroxy hydromorphone and dihydromorphone by heating an aqueous mixture of said salt, 8-hydroxy hydromorphone and dihydromorphone for a time sufficient to reduce the concentration of 8-hydroxy hydromorphone to less than about 1.0%.

19. The method of claim 18, wherein said time is sufficient to reduce the concentration of dihydromorphine to less than or equal to about 2.0%.

20. The method of claim 18, wherein said aqueous mixture is obtained by mixing morphine or a salt thereof with an acid in the presence of a catalyst in the substantial absence of hydrogen gas.

21. The method of claim 20, wherein said catalyst comprises non-supported palladium.

22. The method of claim 20, wherein said acid is hydrochloric acid.

23. The method of claims 18, wherein the time is greater than about thirty minutes.

24. The method of claim 23, wherein the time is greater than or equal to about five hours.

25. The method of claim 18, wherein said salt is bisulfite.

26. The method of claim 18, wherein said pharmaceutical composition comprises hydromorphone and:

a) from about 0.05% up to about 1.0% dihydromorphine;

b) up to about 0.1% morphine;

c) up to about 0.8% 8-hydroxy hydromorphone;

d) up to about 0.5% bis-hydromorphone; and e) up to about 0.2% other impurities.

27. The composition of claim 16, wherein said composition is prepared by a process comprising heating an aqueous mixture of hydromorphone salt, 8-hydroxy hydromorphone and dihydromorphone for a time sufficient to reduce the concentration of 8-hydroxy hydromorphone to less than about 1.0%.

28. The composition of claim 27, comprising hydromorphone and:

a) from about 0.05% up to about 1.0% dihydromorphine;

b) up to about 0.1% morphine;

c) up to about 0.8% 8-hydroxy hydromorphone;

d) up to about 0.5% bis-hydromorphone; and e) up to about 0.2% other impurities.

29. The composition of claim 27, wherein said acid is hydrochloric acid and said catalyst is non-supported palladium.

* * * * *